(12) United States Patent
Weber et al.

(10) Patent No.: US 6,764,678 B2
(45) Date of Patent: Jul. 20, 2004

(54) LOCAL ANESTHETIC METHODS AND KITS

(75) Inventors: Eckard Weber, San Diego, CA (US); Howard I. Katz, La Jolla, CA (US)

(73) Assignee: Novalar Pharmaceuticals, Inc., DE (US)

( * ) Notice: Subject to any disclaimer, the term of this patent is extended or adjusted under 35 U.S.C. 154(b) by 0 days.

(21) Appl. No.: 10/155,171

(22) Filed: May 28, 2002

(65) Prior Publication Data

US 2002/0183356 A1 Dec. 5, 2002

Related U.S. Application Data

(62) Division of application No. 09/852,751, filed on May 11, 2001, now Pat. No. 6,432,401.
(60) Provisional application No. 60/203,800, filed on May 12, 2000, and provisional application No. 60/235,855, filed on Sep. 27, 2000.

(51) Int. Cl.[7] .................. A61K 38/46; A61K 31/24; C12N 1/00; A01N 25/00
(52) U.S. Cl. ................ 424/94.62; 435/810; 514/537; 514/816; 514/818
(58) Field of Search ............................ 424/94.62, 94.1; 435/810; 514/537, 816, 818, 304, 649

(56) References Cited

U.S. PATENT DOCUMENTS

| | | | |
|---|---|---|---|
| 4,659,714 A | * 4/1987 | Watt-Smith | |
| 4,888,344 A | 12/1989 | Sunagawa et al. | 514/210 |
| 4,938,870 A | 7/1990 | Butler et al. | 424/678 |
| 5,149,320 A | 9/1992 | Dhaliwal et al. | 604/49 |
| 5,261,903 A | 11/1993 | Dhaliwal et al. | 604/416 |
| 6,001,845 A | 12/1999 | Estok | 514/284 |
| 6,432,401 B2 | 8/2002 | Weber et al. | 424/94.62 |

OTHER PUBLICATIONS

Bernstein, R.M. and Rassman, W.R., "Limiting epinephrine in large hair transplant sessions," *Hair Transplant Forum International 10:39–42*, New Hair Institute, Inc. (Mar.–Apr. 2000), accessed on Aug. 23, 2002 <http://www.800newhair.com/medical_publications/limiting_epinephrine.html>.

Pimentel, L.A.S. and Goldenburg, R.C.d.S., "Local Injection of Hyaluronidase in Increasing Skin Flap Survival: An Experimental Study," *Revista da Sociedade Brasileira de Cirurgia Plastica 14:49–55*, Sociedade Brasileira de Cirurgia Plastica (1999), accessed on Aug. 15, 2000 <http://www.sbcp.org/revista/voll4_nl/pimentel/english.html>.

Robertson, V.J. et al., "Quantitative and qualitative analysis of the pressor effects of levonordefrin," *J. Cardiovasc. Pharmacol.* 6:929–935, Lippincott, Williams, & Wilkins (1984).

Swinyard, E.A., "Local Anesthetics," in *Remington's Pharmaceutical Sciences*, Osol, A. et al., eds., Mack Publishing Co., Easton, PA, pp. 991–1003 (1980).

International Search Report for International Application No. PCT/US01/40711, mailed Oct. 11, 2001.

* cited by examiner

Primary Examiner—Christopher R. Tate
Assistant Examiner—Randall Winston
(74) Attorney, Agent, or Firm—Sterne, Kessler, Goldstein & Fox P.L.L.C.

(57) ABSTRACT

Methods of reversing local anesthesia are disclosed. The methods comprise administering a local anesthetic and alpha adrenergic receptor agonist to induce local anesthesia followed by reversing anesthesia with a low dose of an alpha adrenergic receptor antagonist. Also disclosed are kits comprising a local anesthetic, an alpha adrenergic receptor agonist and a low dose of an alpha adrenergic receptor antagonist.

31 Claims, No Drawings

LOCAL ANESTHETIC METHODS AND KITS

This application is a divisional of U.S. patent application Ser. No. 09/852,751, filed May 11, 2001, now allowed as U.S. Pat. No. 6,432,401, claiming priority from U.S. Provisional Application Nos. 60/203,800 and 60/235,855, filed May 12, 2000 and Sep. 27, 2000, respectively, now abandoned. The entirety of each of these applications is incorporated by reference herein.

FIELD OF THE INVENTION

The invention is in the field of medicinal chemistry. The invention relates in particular to a method of reversing local anesthesia induced by a local anesthetic and an alpha-adrenergic agonist, comprising administering an effective low dose of an alpha-adrenergic antagonist.

RELATED ART

Local anesthesia is widely used by dentists to provide pain relief to patients during dental procedures. To provide pain relief, a drug formulation containing a local anesthetic compound such as lidocaine is injected into the gum tissue surrounding the tooth or teeth on which the dental procedure is to be performed. There are short-acting and long-lasting local anesthetic drug formulations. Short-acting local anesthetic drug formulations contain lidocaine or a related local anesthetic drug dissolved in saline or other suitable injection vehicle. Typically, local anesthesia with short-acting local anesthetics lasts approximately 20–30 minutes, which is not long enough for many dental procedures. To obtain long-lasting local anesthesia, dentists often use lidocaine or other local anesthetic formulations which, in addition to the local anesthetic drug itself, contain low concentrations of epinephrine or another adrenergic receptor agonist such as levonordefrin. More than 90% of the local anesthesia procedures performed by dentists involve local anesthetic formulations containing alpha-adrenergic receptor agonists. The vasoconstrictor is necessary because local anesthetics without vasoconstrictor are too short-acting for most dental procedures. The added epinephrine stimulates alpha-adrenergic receptors on the blood vessels in the injected tissue. This has the effect of constricting the blood vessels in the tissue. The blood vessel constriction causes the local anesthetic to stay in the tissue much longer, resulting in a large increase in the duration of the anesthetic effect (from 20 minutes for the short-acting formulation to 3–6 hours for the long-lasting formulation). A major problem with the use of epinephrine-containing local anesthetics is soft-tissue anesthesia (lip, cheek, tongue) which usually lasts many hours longer than anesthesia and analgesia of the tooth pulp. Tooth pulp anesthesia and analgesia are the desired effects of local anesthesia from a dental procedural perspective while soft-tissue anesthesia is usually an undesirable side effect. Soft tissue anesthesia results in a number of problems and inconveniences, such as a prolonged and uncomfortable feeling of numbness in and around the mouth, inability to smile, difficulty eating, drinking and swallowing, loss of productivity by missing work hours or meetings etc. Lingering soft-tissue anesthesia can be the cause of injuries due to biting of the tongue or lips. Lingering soft-tissue anesthesia can also result in loss of productivity due to missed work hours or meetings etc. Furthermore, lingering soft-tissue anesthesia is an inconvenience and it is perceived as an annoyance by many patients. Lingering soft-tissue anesthesia can lead to injury especially in children who often bite into the anesthetized tissue out of curiosity. It would therefore be desirable to have a drug that could be used at will by dentists to rapidly reverse local anesthesia after it is no longer needed.

U.S. Pat. No. 4,659,714 discloses a method of prolonging local anesthesia by coadministering a vasoconstrictor, in particular, a vasoconstrictor that acts upon the alpha-adrenergic receptor sites of the blood vessel walls. The '714 patent also discloses the subsequent administration of an alpha-adrenergic receptor antagonist to cause reduction of the prolonged anesthesia effect. Included within the group of alpha-adrenergic receptor antagonists described in this patent are phentolamine mesylate. However, the examples make reference to the administration of "phentolamine." It is much more likely that what was administered was phentolamine mesylate since phentolamine mesylate is FDA approved and readily soluble in water. In contrast, phentolamine is not FDA approved and is relatively insoluble in water.

As shown in Example 1, Table 1, 0.5–1.5 mg of "phentolamine" was administered to groups of patients which were pretreated with lignocaine admixed with epinephrine. The results in Table 1 show a reduction in the duration of anesthesia with increasing amounts of "phentolamine." In Example 2, 2 mg of "phentolamine" was administered. In Example 3, four injections of 1 mg each (4 mg total) of "phentolamine" were administered. In Example 4, four injections of 1 mg each (4 mg total) of "phentolamine" were administered.

The drug doses of "phentolamine" described in the '714 patent (0.5–4 mg) overlap the doses of phentolamine mesylate that are approved by the FDA for the systemic treatment of high blood pressure in patients with pheochromocytoma (total dose of 5 mg in a solution of 2.5–5 mg/ml). Since those doses are normally intended for systemic treatment of high blood pressure, those high dose levels can cause severe side effects when used in healthy, normal people. The package insert of the phentolamine-mesylate product states the following side effect warning: "Myocardial infarction, cerebrovascular spasm, and cerebrovascular occlusion have been reported to occur following the administration of phentolamine, usually in association with marked hypotensive episodes." Thus, the drug doses taught by the '714 patent for the reversal of local anesthesia may cause unacceptable side effects, precluding the use of this product for anesthesia reversal in healthy normal subjects in a dentist's office.

It has now been discovered that a highly effective local anesthesia reversal can be obtained by injections of much lower concentrations of phentolamine-mesylate than is disclosed in the '714 patent. It has been found that a solution containing only 0.05 mg/ml of phentolamine-mesylate can rapidly reverse the effect of a local anesthetic containing an alpha adrenergic receptor agonist. This phentolamine-mesylate drug concentration is 20–100 times lower than the phentolamine-mesylate drug concentration taught by the '714 patent. The advantage is that, at such low phentolamine-mesylate drug concentrations, no systemic side effects such as myocardial infarction and cerebrovascular spasm will be observed. This allows the safe and effective use of phentolamine-mesylate for local anesthesia reversal without causing life-threatening or other untoward side effects. Indeed, in a human clinical efficacy study using a low-concentration-formulation of phentolamine-mesylate, a highly effective anesthesia reversal was observed without any side-effects whatsoever. Thus, this invention constitutes a crucial improvement of the local anesthesia reversal method taught by the '714 patent.

SUMMARY OF THE INVENTION

The present invention provides compositions and formulations of low concentrations of phentolamine-mesylate and other alpha adrenergic receptor antagonists and use thereof for reversing the effects of long-lasting local anesthetic agents containing alpha-adrenergic receptor agonists.

In particular, the invention relates to a method of providing local anesthesia to a mammal, comprising:

(a) administering to the mammal in need thereof an anesthetic agent and an alpha adrenergic receptor agonist to the site to be anesthetized, wherein said anesthetic agent is administered in an amount effective to provide local anesthesia and said alpha adrenergic receptor agonist is administered in an amount effective to constrict the blood vessels at the site and prolong the local anesthesia, and then (b) administering a low dose of an alpha adrenergic receptor antagonist to said site to reduce the prolongation.

In a preferred embodiment, the invention relates to a method of providing local anesthesia to a human, comprising:

(a) administering to a human in need thereof by injection to the site to be anesthetized a solution comprising polocaine and levonordefrin, wherein said polocaine is administered in an amount effective to provide local anesthesia and said levonerdefrin is administered in an amount effective to constrict the blood vessels at the site and prolong the local anesthesia, thereby producing local anesthesia at said site, (b) carrying out a medical procedure on the human, and then (c) administering phentolamine mesylate at said site at a concentration of about 0.05 mg/ml or less to reduce the prolongation.

The invention also relates to a method of enhancing the survival of a tissue graft, comprising (a) administering to a mammal undergoing a tissue graft an anesthetic agent and an alpha adrenergic receptor agonist to the site of the tissue graft, wherein said anesthetic agent is administered in an amount effective to provide local anesthesia and said alpha adrenergic receptor agonist is administered in an amount effective to constrict the blood vessels at the site and prolong the local anesthesia, (b) performing the tissue graft procedure, and then (c) administering an alpha adrenergic receptor antagonist to said site to reduce the prolongation and enhance the tissue graft survival.

The invention also relates to a method of providing a regional anesthetic block to a mammal, comprising:

(a) administering to the mammal in need thereof an anesthetic agent and an alpha adrenergic receptor agonist in the site to receive the anesthetic block, wherein said anesthetic agent is administered in an amount effective to provide local anesthesia and said alpha adrenergic receptor agonist is administered in an amount effective to constrict the blood vessels in the site and prolong the anesthetic block, and then (b) administering an alpha adrenergic receptor antagonist to said site to reduce the prolongation.

The invention also relates to a kit comprising a carrier means having in close confinement therein two or more container means, wherein a first container means contains an anesthetic agent and optionally an alpha adrenergic receptor agonist and a second container means contains a low dose of an alpha adrenergic receptor antagonist.

DESCRIPTION OF PREFERRED EMBODIMENTS

The invention relates to a method of providing local anesthesia to a mammal, comprising:

(a) administering to the mammal in need thereof an anesthetic agent and an alpha adrenergic receptor agonist to the site to be anesthetized, wherein said anesthetic agent is administered in an amount effective to provide local anesthesia and said an alpha adrenergic receptor agonist is administered in an amount effective to constrict the blood vessels at the site and prolong the local anesthesia, and then (b) administering a low dose of an alpha adrenergic receptor antagonist to said site to reduce the prolongation.

The anesthetic agent and alpha adrenergic receptor agonist may be administered together as part of a unitary pharmaceutical composition or as part of separate pharmaceutical compositions so long as the alpha adrenergic receptor agonist acts to constrict the blood vessels in the vicinity of where the anesthetic agent has been administered to result in a prolonging of anesthesia. In a preferred embodiment, the anesthetic agent and alpha adrenergic receptor agonist are administered together in solution. The anesthetic agent and alpha adrenergic agonist may be administered by injection, by infiltration or by topical administration, e.g. as part of a gel or paste.

In a preferred embodiment, a solution comprising the anesthetic agent and alpha adrenergic receptor agonist is administered by injection directly into the site to be anesthetized, e.g. prior to a dental procedure.

Examples of local anesthetics that may be used in the practice of the invention include without limitation lidocaine, polocaine, lignocaine, xylocaine, novocaine, carbocaine, etidocaine, procaine, prilocaine, bupivacaine, cinchocaine and mepivacaine.

Examples of alpha adrenergic receptor agonists that can be used according to the invention include catecholamines and catecholamine derivatives. Particular examples include without limitation levonordefrin, epinephrine, and norepinephrine.

Examples of alpha adrenergic receptor antagonists that can be used in the practice of the invention include without limitation phentolamine, phentolamine hydrochloride, phentolamine mesylate, tolazoline, yohimbine, rauwolscine, doxazosine, labetolol, prazosine, tetrazosine and trimazosine. Phentolamine-mesylate is approved by the FDA for the treatment of hypertension in patients with pheochromocytoma, for the treatment of dermal necrosis and sloughing following accidental extravasation of norepinephrine, and for the diagnosis of pheochromocytoma (phentolamine blocking test). The drug is supplied in vials containing 5 mg of drug substance which may be dissolved in physiological saline or other pharmaceutically acceptable carrier.

In order to reverse the local anesthesia after a medical procedure according to the present invention, the alpha adrenergic receptor antagonist is administered at a low dose, i.e. at a dose that does not cause side effects, i.e. at or below about 0.25 mg per dose for adults (at or below about 0.0036 mg/kg) or 0.1 mg per dose for children, more preferably, below about 0.1 mg per dose for adults (below about 0.0014 mg/kg) or 0.04 mg per dose for children, most preferably, at about 0.08 mg per dose for adults (about 0.0011 mg/kg) or about 0.032 mg per dose for children, of phentolamine mesylate or a molar equivalent of another adrenergic receptor antagonist. In a preferred embodiment, the alpha adrenergic receptor antagonist is present at a concentration of from about 0.001 mg/ml to about 0.25 mg/ml, more preferably, about 0.05 mg/ml to about 0.1 mg/ml.

The alpha adrenergic receptor antagonist may be administered by injection into the site of anesthesia, by infiltration or by topical administration. In a preferred embodiment, the alpha adrenergic receptor antagonist is administered to mucosal tissue. In this embodiment, the alpha adrenergic receptor antagonist may be applied to the site in the form of an impregnated wafer, pellet or cotton ball, whereby the antagonist is taken up by the mucosal tissue resulting in reversal of the anesthesia. In another embodiment, the alpha adrenergic receptor antagonist is administered to the site of a regional anesthetic block to reverse the block, e.g. by injection or infiltration into the site. In a preferred embodiment, the alpha adrenergic receptor antagonist is administered via a cannula into the epidural space of an animal to reverse epidural anesthesia.

Examples of medical procedures that may be carried out according to the present invention include, without limitation, both major and minor surgery, dental procedures, cosmetic surgery, tissue grafting (e.g. hair and bone grafting) and cesarean section. In one embodiment, reversal of anesthesia according to the present invention is carried out by medical trainees to mitigate any mistakes that are made, and which may lead to the loss of extremities such as fingers, as well as ears and tips of noses.

Hyaluronidase, an enzyme which enhances the diffusion of drugs within tissues, may be administered together with the alpha adrenergic receptor antagonist. The hyaluronidase and alpha adrenergic receptor antagonist may be administered together as part of a unitary pharmaceutical composition or as part of separate pharmaceutical compositions, so long as the hyaluronidase and alpha adrenergic receptor antagonist are administered to the site where anesthesia is to be reversed and are present in amounts effective to enhance the diffusion of the alpha adrenergic receptor antagonist and to reverse the anesthesia, respectively. The hyaluronidase is administered one or more times into the site of anesthesia. In general, about 1.5 U to about 200U of hyaluronidase is administered in one or more injections. In a most preferred embodiment, about 200 U of hyaluronidase is administered by injection into the site. Those of ordinary skill in the art can determine optimal amounts of hyaluronidase with no more than routine experimentation.

When performing hair grafts, the surgeon often injects an anesthetic and epinephrine to reduce bleeding and provide a clear vision of the site. According to Bernstein, R. M. and Rassman, W. R., Hair Transplant Forum International 10:39–42 (2000), the usefulness of epinephrine in hair graft procedures is limited by a number of factors including post-operative telogen effluvium when epinephrine is used in large transplant sessions. In addition, when adrenaline is added to an area whose blood supply is already compromised by a large number of recipient sites, the tissue may not receive enough oxygen. Although not proven, according to Bernstein and Rassman it is likely that epinephrine infiltration into the recipient area is a contributing factor in the development of the "central necrosis" that has occasionally been reported during hair transplantation. Furthermore, it is possible that the intense vasoconstrictive action of epinephrine may contribute to the decreased graft survival. Thus, according to the present invention, one may achieve enhanced tissue graft survival in a method comprising (a) administering to a mammal undergoing a tissue graft an anesthetic agent and an alpha adrenergic receptor agonist to the site of the tissue graft, wherein the anesthetic agent is administered in an amount effective to provide local anesthesia and the an alpha adrenergic receptor agonist is administered in an amount effective to constrict the blood vessels at the site and prolong the local anesthesia, (b) performing the tissue graft procedure, and then (c) administering an alpha adrenergic receptor antagonist to said site to reduce the prolongation and enhance the tissue graft survival.

In a preferred embodiment, the tissue graft is a hair graft. In another preferred embodiment, a low dose of alpha adrenergic receptor antagonist is administered to the site to avoid untoward side effects.

Such hair grafts include skin flaps containing a plurality of hair cells and single transplanted hair cell follicles. Typically, such hair grafts are obtained from a site on the animal that has actively growing hair. According to the present invention, an alpha adrenergic receptor antagonist is administered after a hair graft procedure to reverse the local anesthesia and reduce post-operative telogen effluvium (shedding of hair) and survival of the skin flap.

In another embodiment, hyaluronidase may be administered to the tissue graft site to increase survival of the graft. According to Pimentel, L. A. S. and Goldenburg, R. C. d.S, Revista da Soociedade Brasileira de Cirurgia Plastica 14 (1999), the local administration of hyaluronidase increases skin flap survival. According to the authors, hyaluronidase is an enzyme that reduces or prevents tissue injury presumably by causing the rapid diffusion of extravasated fluids to distant areas, thus allowing a better turnover of nutrients. The hyaluronidase is generally injected one or more times into the site of the hair graft. Similarly, the present invention can be used to improve survival of other engrafted tissues or bone in any graft surgical procedure where a local anesthetic and an alpha adrenergic receptor agonist is used minimize bleeding during the surgery and where subsequent rapid reperfusion of tissue is desired in order to increase graft survival.

In a further embodiment, an alpha adrenergic receptor antagonist is administered after a regional anesthetic block to reverse the block. Epidural anesthesia is commonly administered to provide a regional anesthetic block in a number of medical procedures including child birth, cesarean section, surgery to the pelvis and the like. Prolonged epidural anesthesia has many untoward side effects, including prolonged paralysis, inability to voluntarily urinate, and hypotension. Typically, the anesthesiologist injects into the epidural space an equal volume of saline in an effort to dilute the anesthetic and reduce the anesthesia.

The present invention solves the side effect problems by providing for on demand reversal of the anesthesia without the need for injecting large volumes of saline. In this embodiment, the invention relates to a method of providing a regional anesthetic block to a mammal, comprising:

(a) administering to a mammal in need thereof an anesthetic agent and an alpha adrenergic receptor agonist in the site to receive the anesthetic block, wherein the anesthetic agent is administered in an amount effective to provide local anesthesia and the alpha adrenergic receptor agonist is administered in an amount effective to constrict the blood vessels in the site and prolong the local anesthesia, and then (b) administering an alpha adrenergic receptor antagonist to the site to reduce the prolongation.

In a preferred embodiment, a low dose of the alpha adrenergic receptor antagonist is administered. In another preferred embodiment, the anesthetic block is epidural anesthesia and the site of the block is the epidural space. The invention has application to reversal of other blocks as well including brachial plexus and femoral blocks.

In another embodiment, hyaluronidase is administered together with the alpha adrenergic receptor antagonist to enhance the diffusion of the alpha adrenergic receptor antagonist within the site of the block, e.g. the epidural space, and speed reversal of the anesthesia.

The invention also relates to a kit comprising a carrier means such as a carton or box having in close confinement therein two or more container means such as carpules, vials, tubes, jars and the like. A first container means contains an anesthetic agent and optionally an alpha adrenergic receptor agonist and a second container means contains a low dose of an alpha adrenergic receptor antagonist. Alternatively, the alpha adrenergic receptor agonist may be present in a separate container means. A further container means may contain hyaluronidase. Alternatively, the hyaluronidase is in the same container means as the alpha adrenergic receptor antagonist. In a preferred embodiment, the anesthetic agent, alpha adrenergic receptor agonist, alpha adrenergic receptor antagonist and, optionally, the hyaluronidase are present in 1.8 mL carpules that fit into a standard dental local anesthetic syringe. Such carpules are available commercially from a variety of suppliers, e.g. Henry Schein, Port Washington, N.Y. In this embodiment, a carpule containing the local anesthetic and alpha adrenergic receptor agonists is placed into the syringe, and the mixture is injected. The carpule may then be removed and a second carpule inserted which contains the alpha adrenergic receptor antagonist and, optionally, the hyaluronidase.

The anesthetic agent, vasoconstrictor, alpha adrenergic receptor antagonist and, optionally, the hyaluronidase may be present in solution, preferably, a sterile solution, optionally containing salts and buffers, or as part of a gel or paste for topical administration. See U.S. Pat. No. 4,938,970 and Remington's Pharmaceutical Sciences, A. Osol (ed.), 16th Edition, Mack Publishing Co., Easton, Pa. (1980).

Mammals which may be treated according to the present invention include all mammals that may experience the beneficial effects of the present invention. Such mammals include without limitation humans and veterinary mammals such as cattle, pigs, sheep, horses, dogs, and cats. When applied to children and veterinary animals, the prompt reversal of anesthesia inhibits the child or animal from tearing open fresh sutures.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLES

Study Rationale and Purpose

Local anesthesia is widely used by dentists to effect anesthesia during dental procedures. Local anesthetics often contain alpha-adrenergic receptor agonists to cause vasoconstriction thereby prolonging anesthesia. The vasoconstrictor is necessary because local anesthetics without vasoconstrictor are too short-acting for most dental procedures. On the other hand, in many instances the prolonged local anesthetic effect lasts much longer than required for many dental procedures. It would be desirable to have a drug that could be used at will to rapidly reverse local anesthesia after it is no longer needed. Lingering local anesthesia can be the cause of injuries due to biting of the tongue or lips. Lingering local anesthesia can also result in loss of productivity due to missed work hours. Lastly, lingering local anesthesia is an inconvenience and it is perceived as an annoyance by many patients. The purpose of the present study was to determine whether phentolamine-mesylate, an injectable alpha-adrenergic receptor agonist, which is FDA approved for the systemic treatment of hypertension in pheochromocytoma patients, rapidly reverses prolonged local anesthesia when injected locally at a very low concentration. The phentolamine-mesylate concentration chosen for the present study was so low that it would be expected to lack systemic side-effects such as severe episodes of hypotension that have been described with the high systemic drug doses which are approved by the FDA for the treatment of hypertension in pheochromocytoma patients.

Study Design

The present human subjects study was designed to determine whether injection of a physiological saline solution containing an extremely low concentration of phentolamine-mesylate is able to accelerate the reversal of the effects of a previously injected local anesthetic agent containing an alpha-adrenergic receptor agonist. An injection of the physiological saline vehicle (without phentolamine-mesylate) served as the control. In order to compare the effects of phentolamine-mesylate to the vehicle in the same patient, bilateral local anesthesia injections were made into the mouth of the same patient. This was followed by injection of the phentolamine-mesylate containing local anesthetic reversal agent (LARA) into one side of the oral cavity, and injection of the saline vehicle (control) solution into the opposite side of the oral cavity. The time to reversal of the local anesthetic effect on both sides was then recorded to determine whether there is a difference between the two sides.

Drugs

The local anesthetic used was 2% polocaine (mepivacaine hydrochloride) with levonordefrin (1:20,000–0.05 mg/ml) (levonordefrin injection, USP) (Astra USA, Inc., Westborough, Mass. 01581). Levonordefrin is a sympathomimetic amine with a pharmacological profile similar to that of epinephrine, but with a lower potency. The local anesthetic reversal agent (LARA) was prepared as follows: A standard vial containing 5 mg of lyophilized phentolamine-mesylate for injection, USP (Bedford Laboratories, Bedford, Ohio 44146) was reconstituted with 1 ml of physiological saline using a sterile, disposable 3 ml syringe and a sterile disposable hypodermic needle. After dissolution of the lyophilized powder, 0.5 ml of the phentolamine-mesylate solution was withdrawn and injected into a 50 ml vial of physiological saline for injection (USP) by means of a sterile disposable 3 ml syringe and a sterile disposable hypodermic needle. The resulting LARA thus consisted of 0.05 mg/ml phentolamine-mesylate in physiological saline.

Methods

Three healthy, male human subjects, age 34–50, volunteered to have local anesthetic injected in the mouth bilaterally under the lip in an easily repeatable location. The exact time of each injection was recorded. The position chosen was above (apical) the prominence of the root of the upper cuspid teeth. This is a common site selected to numb the cuspids, lateral incisors and upper lip. The volume of the local anesthetic injected was 1.7+0.1 ml on each side of the mouth. Twenty minutes after the local anesthetic was injected, each subject was re-injected with 1.6 ml of LARA on one side and 1.6 ml of physiological saline on the opposite side. A different size needle was used for the anesthetic and LARA or saline. A longer needle (1¼") was used for the local anesthetic resulting in more solution being deposited around the infra-orbital nerves. LARA or saline were injected with a shorter needle (½") resulting in less LARA coming into contact with the anesthetic agent around the infra-orbital nerves. After all subjects received anesthetic agent followed by LARA or saline, the subjects were asked to test the intensity of numbness on both sides at the following sites in the mouth and face: teeth, nose, upper lip and gingiva. Numbness of the teeth was tested by biting or grinding. Lip numbness was tested with the touch of the finger or tongue, and nose numbness was tested with the touch of the finger. Gingiva numbness was tested with the blunt end of a wooden cotton swab.

Blinding

Two of the subjects (E and M) were blinded with respect to the side of the mouth where LARA or saline vehicle were injected, i.e. the subjects were not told by the PI which side received LARA and which side received saline vehicle. The third subject (H) was the PI of the study who injected himself. As a consequence, subject H was not blinded with respect to the side at which LARA or saline were injected.

Results

In all three subjects there was a dramatic acceleration of local anesthesia reversal on the side that had been injected with LARA compared to the side that had been injected with saline. No side-effects of any kind were noted in any of the three subjects. In general, feeling to the teeth returned first. Table 1 shows the times at which numbness disappeared and sensations re-appeared in the three subjects at the various sites on both sides of the mouth and face. In the early stages of recovery the subjects reported that it was somewhat difficult to determine which side of the lip was recovering first. In the later stages of recovery, however, the differences between the two sides of the lip were profound and dramatic. In the other parts of the mouth and face, lateral differences were reported to be pronounced even in the very early stages of recovery. The difficulty to sense lateral differences in the lips between the two sides early in the recovery process is thought to be due to the following fact: The labial branches of the infra-orbital nerve decussate at the midline, resulting in a crossover of innervation (and resulting sensation) at the midline of the upper lip.

TABLE 1

| Site of anesthesia | Recovery Time RHS (Minutes) | Recovery Time LHS (Minutes) |
|---|---|---|
| Subject E - LARA on right hand side (RHS), Vehicle on LHS | | |
| Teeth 80% Recovered | 21 | 85 |
| Teeth Fully Recovered | 28 | 101 |
| Nose | 30 | 143 |
| Lip | 41 | 83 |
| Gingiva | 46 | 141 |

| Site of anesthesia | Recovery Time LHS (Minutes) | Recovery Time RHS (Minutes) |
|---|---|---|
| Subject M - LARA on LHS, Vehicle on RHS | | |
| Teeth | 32 | 121 |
| Nose | 40 | 163 |
| Gingiva | 45 | 102 |
| Lip | 36 | 178 |
| All Sensation | 58 | 229 |

| Site of anesthesia | Recovery Time RHS (Minutes) | Recovery Time LHS (Minutes) |
|---|---|---|
| Subject H - LARA on RHS, Vehicle on LHS | | |
| Teeth 80% Recovered | 19 | 201 |
| Teeth 100% Recovered | 27 | 218 |
| Gingiva | 42 | 137 |
| Lip | 37 | 226 |
| Nose | 25 | 140 |
| All Sensation | 58 | 263 |

Conclusion

LARA had a profoundly faster effect on removing the numbness associated with local anesthesia than using physiological saline. The total amount of phentolamine-mesylate contained in the administered LARA solution was 0.08 mg (1.6 ml of a 0.05 mg/ml solution). This total dose of phentolamine-mesylate is approximately 62 times lower than the 5 mg dose approved by the FDA for systemic treatment of hypertension in pheochromocytoma patients (1 ml of a 5 mg/ml solution) and which can cause severe episodes of hypotension in normal patients. At the extremely low efficacious doses found to be effective in the present study, any systemic side effects, such as those that can occur with the FDA-approved high dose, are likely to be absent. Indeed, in the present study, no side-effects of any kind were noted during or after administration of 0.05 mg/ml phentolamine-mesylate.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A method of providing local anesthesia to a mammal, comprising:
   (a) administering to said mammal in need thereof an anesthetic agent and an alpha adrenergic receptor agonist to the site to be anesthetized, wherein said anesthetic agent is administered in an amount effective to provide local anesthesia and said alpha adrenergic receptor agonist is administered in an amount effective to constrict the blood vessels at the site and prolong the local anesthesia, and then
   (b) administering a unit dose of a composition to said site, said unit dose comprising between about 0.00 18 mg and about 0.45 mg phentolamine mesylate or a molar equivalent of another alpha adrenergic receptor antagonist and a pharmaceutically acceptable carrier.

2. The method of claim 1, wherein said anesthetic agent and said alpha adrenergic receptor agonist are administered together in solution.

3. The method of claim 2, wherein said anesthetic agent and said alpha adrenergic receptor agonist are administered together in solution from a standard dental local anesthetic syringe.

4. The method of claim 1, wherein said anesthetic agent is selected from the group consisting of lidocaine, polocaine, etidocaine, lignocaine, xylocaine, novocaine, carbocaine, procaine, prilocaine, bupivacaine, cinchocaine, and mepivacaine.

5. The method of claim 1, wherein said alpha adrenergic receptor agonist is levonordefrin, epinephrine, or norepinephrine.

6. The method of claim 1, wherein said unit dose comprises between about 0.09 mg and about 0.45 mg phentolamine mesylate or a molar equivalent of another alpha adrenergic receptor antagonist.

7. The method of claim 1, wherein said composition is a solution formulated for administration to a mammal by injection, infiltration, or topical application.

8. The method of claim 7, wherein said solution is formulated for topical application to mucosal tissue.

9. The method of claim 8, wherein said solution is used to impregnate a wafer, pellet, or cotton ball, for application to mucosal tissue.

10. The method of claim 1, wherein said composition is a gel or a paste formulated for topical administration to a mammal.

11. The method of claim 10, wherein said composition is formulated for topical application to mucosal tissue.

12. The method of claim 1, wherein said alpha adrenergic receptor antagonist is selected from the group consisting of phentolamine, phentolamine hydrochloride, phentolamine mesylate, tolazoline, yohimbine, rauwolscine, doxazosine, labetalol, prazosine, tetrazosine and trimazosine.

13. The method of claim 12, wherein said alpha adrenergic receptor antagonist is phentolamine mesylate.

14. The method of claim 1, wherein said unit dose is present in a container that fits into a standard dental local anesthetic syringe.

15. The method of claim 14, wherein said container has a volume of between 1.6 ml and 1.8 ml.

16. The method of claim 1, wherein said unit dose comprises phentolamine mesylate, and wherein said unit dose is present in a container that fits into a standard dental local anesthetic syringe.

17. A method of providing a regional anesthetic block to a mammal, comprising:
  (a) administering to said mammal in need thereof an anesthetic agent and an alpha adrenergic receptor agonist to the site to receive the anesthetic block, wherein said anesthetic agent is administered in an amount effective to provide local anesthesia and said alpha adrenergic receptor agonist is administered in an amount effective to constrict the blood vessels at the site and prolong the anesthetic block, and then
  (b) administering a unit dose of a composition to said site, said unit dose comprising between about 0.0018 mg and about 0.45 mg phentolamine mesylate or a molar equivalent of another alpha adrenergic receptor antagonist and a pharmaceutically acceptable carrier.

18. The method of claim 17, wherein said site is the epidural space.

19. The method of claim 17, wherein said anesthetic agent and said alpha adrenergic receptor agonist are administered together in solution.

20. The method of claim 19, wherein said solution is administered by injection into the site.

21. The method of claim wherein said anesthetic agent is selected from the group consisting of lidocaine, polocaine, etidocaine, lignocaine, xylocaine, novocaine, carbocaine, procaine, prilocaine, bupivacaine, cinchocaine, and mepivacaine.

22. The method of claim 17, wherein said alpha adrenergic receptor agonist is levonordefrin, epinephrine, or norepinephrine.

23. The method of claim 17, wherein said unit dose comprises between about 0.09 mg and about 0.45 mg phentolamine mesylate or a molar equivalent of another alpha adrenergic receptor antagonist.

24. The method of claim 17, wherein said composition is a solution formulated for administration to a mammal by injection, infiltration, or topical application.

25. The method of claim 24, wherein said solution is formulated for topical application to mucosal tissue.

26. The method of claim 25, wherein said solution is used to impregnate a wafer, pellet, or cotton ball, for application to mucosal tissue.

27. The method of claim 17, wherein said composition is a gel or a paste formulated for topical administration to a mammal.

28. The method of claim 27, wherein said composition is formulated for topical application to mucosal tissue.

29. The method of claim 17, wherein said alpha adrenergic receptor antagonist is selected from the group consisting of phentolamine, phentolamine hydrochloride, phentolamine mesylate, tolazoline, yohimbine, rauwolscine, doxazosine, labetalol, prazosine, tetrazosine and trimazosine.

30. The method of claim 29, wherein said alpha adrenergic receptor antagonist is phentolamine mesylate.

31. The method of claim 17, wherein said unit dose is present in a container having a volume of between 1.6 ml and 1.8 ml.

* * * * *